United States Patent [19]
Ohashi et al.

[11] 4,416,977
[45] Nov. 22, 1983

[54] SILVER HALIDE PHOTOGRAPHIC PHOTOSENSITIVE MATERIAL

[75] Inventors: Minoru Ohashi; Kiyoshi Futaki; Katsuaki Iwaosa, all of Nagaokakyo, Japan

[73] Assignee: Mitsubishi Paper Mills, Ltd., Tokyo, Japan

[21] Appl. No.: 349,092

[22] Filed: Feb. 16, 1982

[30] Foreign Application Priority Data

Feb. 17, 1981 [JP] Japan .................................. 56-21763

[51] Int. Cl.³ ............................................... G03C 1/34
[52] U.S. Cl. ..................................... 430/446; 430/611; 430/613; 430/448; 430/955; 430/614
[58] Field of Search ............... 430/434, 611, 613, 219, 430/614, 446, 448, 955

[56] References Cited

U.S. PATENT DOCUMENTS 2,948,615  8/1960  Dersch et al. ..................... 430/611
2,981,624  4/1961  Dersch et al. ..................... 430/611
3,674,478  7/1972  Grasshoff et al. ................. 430/611
4,111,697  9/1978  Pollet et al. ...................... 430/611

Primary Examiner—Won H. Louie, Jr.
Attorney, Agent, or Firm—Cushman, Darby & Cushman

[57] ABSTRACT

There is disclosed a silver halide photographic photosensitive material which contains in at least one of silver halide emulsion layers and colloid layers permeable to water through to or out from said emulsion layer at least one compound represented by the following general formula (I):

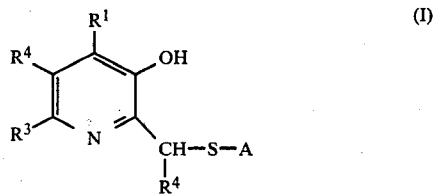

wherein A, $R^1$, $R^2$, $R^3$ and $R^4$ are the same as defined previously. This photosensitive material has stability against over-development fogging.

12 Claims, No Drawings

SILVER HALIDE PHOTOGRAPHIC PHOTOSENSITIVE MATERIAL

BACKGROUND OF THE INVENTION

This invention relates to a photographic photosensitive material comprising a silver halide emulsion layer stabilized against over-development fogging.

When a silver halide photograhic photosensitive material is subjected to developing treatment under severe conditions such as development at comparatively high temperatures or rapid development in a short period of time by the use of a highly active developer (a developer at a high temperature and a high pH), there is a danger of the accompanied reduction of silver halide grains containing entirely no latent image nuclei. The fog produced under the said conditions by the undesired reduction of unexposed silver halide grains manifests itself especially intensely at the end of common development processing and is called over-development fog.

The antifoggants known to be effective in reducing the over-development fog include mercury compounds and heterocyclic mercapto compounds. Although these antifoggants generally reduce the fogging during the course of development or in case of over development, yet, when used in an amount sufficient for the reduction of above-said fogging, they have also a disadvantage of appreciably decreasing the sensitivity of silver halide photosensitive materials. A basic disadvantage of the direct incorporation of heterocyclic mercapto compounds or others which are especially active by themselves against the over-development fogging into a silver halide emulsion originates in the fact that they are active to full extent from the instant of incorporation, that is, they remain active throughout the manufacturing step, shelf period, and the development step; as a consequence they exhibit an undesirable desensitizing effect on the photosensitive material during the manufacture and shelf period thereof.

In order to solve the above problem, attempts have heretofore been made in the art to protect the mercapto group of the aforementioned compounds with a hydrolyzable group, thus rendering the compound inactive during the period wherein its activity is undesirable (throughout the entire period prior to the development processing, including the manufacturing step), and to reactivate the compound by alkaline hydrolysis in the development step. Such substituent groups are generally moieties of thioesters or thioethers of the aforementioned mercapto-type antifoggants.

Regarding the thioester-type substituent, those of the carboxylic acids, sulfonic acids, and carbonic acid derivatives are disclosed in many patents such as, for example, German Pat. No. 1,597,503, U.S. Pat. No. 3,260,597 and German Patent Application "Offenlegungsschrift" No. 2,061,972. Although hydrolyzable in an alkaline developer medium, these thioesters have a disadvantage of being gradually hydrolyzed at least partially also in neutral or weakly acid region. As a consequence, although can be added in inactive form into the emulsion, these thioester-type antifoggants tend to cause undesirable desensitization owing to the partial hydrolysis in the step of emulsion making or during storage of the photosensitive material, if the time span is sufficiently extended.

As contrasted, although the antifoggants having thioester-type substituents, such as, for example, those disclosed in U.S. Pat. Nos. 2,981,624 and 3,260,597 and German Pat. No. 1,173,796 are indeed completely stable in a neutral or weakly acid medium, yet they are unable to prevent effectively the over-development fogging from occurring, because in the development step they are either unable to regenerate the original mercapto-antifoggant or able to regenerate but very slowly.

Further, those compounds disclosed in U.S. Pat. No. 3,674,478 which are able to release a quinone-methide or naphthoquinone-methide and a mercapto-antifoggant in the presence of alkali are indeed able to release quickly the antifoggant in the presence of alkali, but are disadvantageous in that in a weakly acid medium they are unstable to some degree, gradually releasing the antifoggant. As a consequence, if the time interval between the preparation and coating of an emulsion (having a pH in the weakly acid region) is sufficiently long, the antifoggant will be entirely released into the emulsion, causing undesirable desensitization.

SUMMARY OF THE INVENTION

A primary object of this invention, therefore, is to provide an antifoggant (hereinafter referred to as antifoggant precursor) having an inactivated mercapto group which is completely stable in the neutral or weakly acid pH region but is capable of releasing an antifoggant of a predetermined activity in the alkaline pH range (during the developing treatment).

As a result of extensive studies, the present inventors have found that a thioether-type antifoggant precursor represented by the general formula (I) achieves the above-said object of this invention:

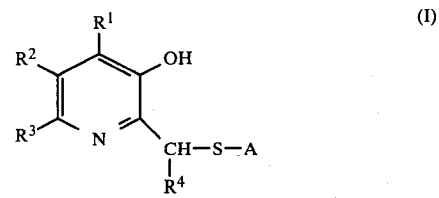

(I)

wherein A represents the heterocyclic group of a mercapto-antifoggant; $R^1$, $R^2$ and $R^3$ represent each a hydrogen atom, halogen atom, alkyl group (preferably an alkyl group having 1 to 10 carbon atoms), or phenyl group; $R^1$ and $R^2$, or $R^2$ and $R^3$ may be bonded to each other to form a benzene ring which may bear a substituent such as an alkyl group, halogen atom, or alkoxy group; and $R^4$ represents a hydrogen atom, alkyl group (preferably an alkyl group having 1 to 5 carbon atoms), or phenyl group.

DESCRIPTION OF PREFERRED EMBODIMENTS

Although the above mercapto-antifoggant may be any of the compounds having an antifoggant activity, yet particularly preferred are 5- or 6-membered nitrogen-containing heterocyclic compounds having a sulfur atom bonded to the carbon atom adjacent to the nuclear nitrogen atom. As the examples of typical hetero rings, mention may be made of tetrazole ring, 1,2,4-triazole ring, benzoxazole ring, benzothiazole ring, benzoimidazole ring, pyridine ring, and pyrimidine ring.

Below are given examples of typical antifoggant precursors represented by the general formula (I), put the invention is not limited thereto.

| Compound No. | |
|---|---|
| 1. | 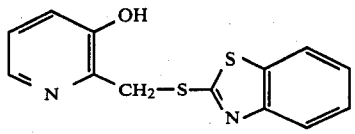 |
| 2. | 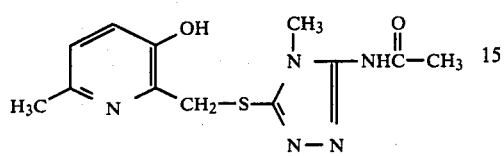 |
| 3. | 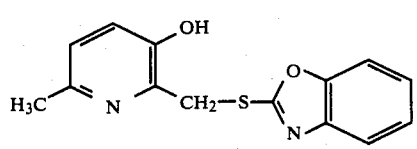 |
| 4. | 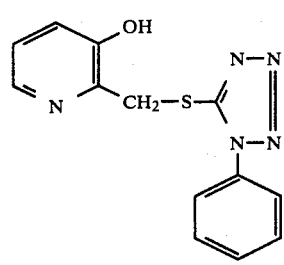 |
| 5. | 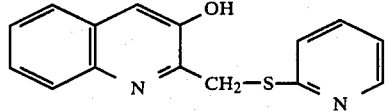 |
| 6. | 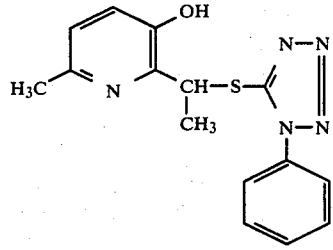 |
| 7. | 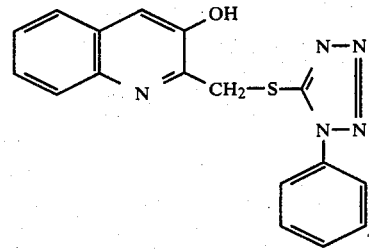 |
-continued
| Compound No. | |
|---|---|
| 8. | 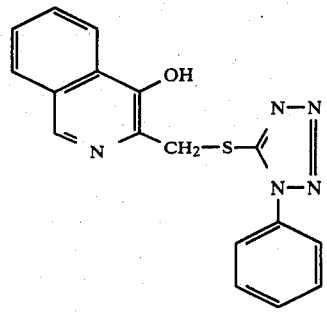 |
| 9. | 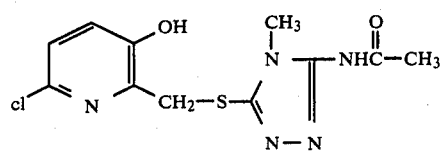 |
| 10. | 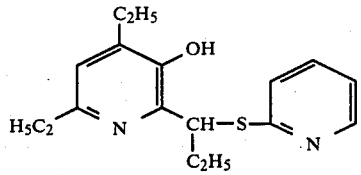 |
| 11. | 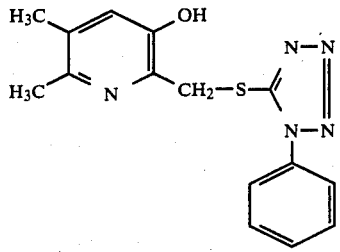 |
| 12. | 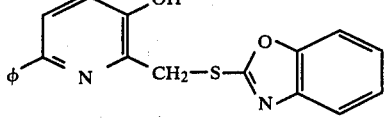 |
| 13. | |
| 14. | |
| 15. | 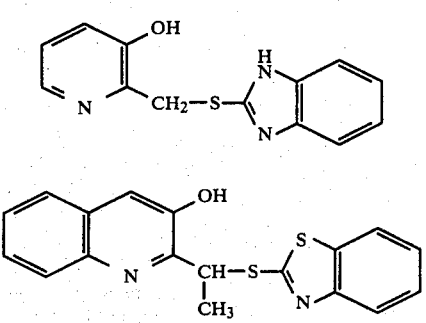 |

| Compound No. | |
|---|---|
| 16. | 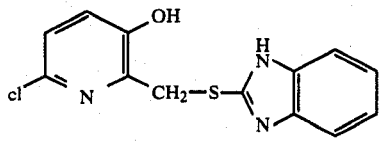 |
| 17. | 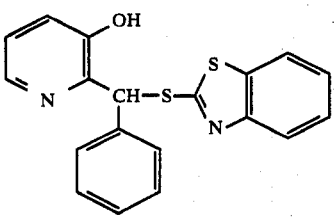 |
| 18. | 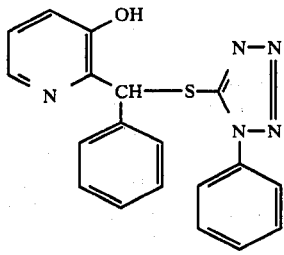 |

As is apparent from the Synthesis Examples given below, the compounds of this invention represented by the general formula (I) are readily obtained by the reaction of a corresponding mercapto-antifoggant with a halogen compound represented by the general formula (II), given below, in the presence of an alkali (e.g. triethylamine).

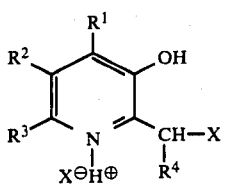

(II)

wherein $R^1$, $R^2$, $R^3$ and $R^4$ are as defined previously and X represents a halogen atom.

With respect to the synthesis, reference is made to J. Am. Chem. Soc., 71, 2969–2972 (1949) and J. Chem. Soc., 1946, 1104–1105.

Below are shown Examples of the synthesis of the present antifoggant precursors.

Synthesis Example 1 (Synthesis of Compound No. 1)

Into 80 ml of DMF, were dissolved 13.5 g of 2-bromomethyl-3-pyridol hydrobromide and 8.4 g of 2-mercaptobenzothiazole. To the solution, was added dropwise while stirring 14 ml of triethylamine over a period of 10 minutes. After completion of the addition, the mixture was stirred for one hour at room temperature. The reaction mixture was poured into about 500 ml of water and extracted with ethyl acetate. The extract was washed with water, dried over anhydrous sodium sulfate and freed from the solvent by distillation under reduced pressure. The residue was recrystallized from methanol. Yield, 11.3 g; melting point, 159.5° C.

| | Elementary analysis: | | |
|---|---|---|---|
| | C % | H % | N % |
| Calculated | 56.91 | 3.67 | 10.21 |
| Found | 56.71 | 3.73 | 10.30 |

Synthesis Example 2 (Synthesis of Compound No. 4)

Into 100 ml of DMF, were dissolved 26.9 g of 2-bromomethyl-3-pyridol hydrobromide and 17.9 g of 1-phenyl-5-mercaptotetrazole. To the solution, was added dropwise while stirring 28.2 ml of triethylamine over a period of 15 minutes. After completion of the addition, the mixture was allowed to react for about 2 hours at room temperature. The reaction mixture was poured into about one liter of water. The precipitated crystals were collected by filtration, washed with water, dried, and recrystallized from methanol; yield, 25.3 g; melting point, 195.5°–196.5° C.

| | Elementary analysis: | | |
|---|---|---|---|
| | C % | H % | N % |
| Calculated | 54.72 | 3.89 | 24.55 |
| Found | 54.75 | 3.75 | 24.64 |

According to this invention, the present antifoggant precursor is incorporated in the silver halide emulsion layer of the photosensitive material or in those colloid layers, such as layers of overcoating or undercoating to the emulsion layer, which are permeable to water through to or out from said emulsion layer. The incorporation of the present antifoggant precursor in the emulsion layer or said colloid layer can be effected by dissolving the antifoggant precursor in a water-miscible solvent such as, for example, DMF, methanol or ethanol and admixing, before coating, into a silver halide emulsion or a colloidal dispersion to be used for said colloid layer. It is also possible to disperse the antifoggant precursor with a latex by means of a technique disclosed in Japanese Patent Application "Kokai" (Laid-open) No. 137,131/78 and admix the dispersion in the silver halide emulsion or the colloid dispersion. The solution or dispersion of the present antifoggant precursor can be incorporated in the silver halide emulsion in any stage of manufacture, but it is preferable to add to the silver halide emulsion just before coating.

The suitable concentration of the present antifoggant precursor varies depending upon the type of compound and its location within the photographic material. In incorporating into the silver halide emulsion, it is added in an amount of 0.1 to 100 millimoles, preferably 0.5 to 50 millimoles for 1 mole of silver halide, whereas it is added in somewhat larger amounts in incorporating into other colloid layers which are in contact with or become in contact with the silver halide emulsion layer in the developing treatment.

After exposure the photosensitive material containing the present antifoggant precursor is developed with common developers. The developed material is stabilized in a common fixing or stabilizing bath.

The present invention is adaptable for any type of silver halide emulsions such as, for example, spectrally sensitized or nonsensitized emulsions, X-ray emulsions, infra red-sensitive emulsions as well as high-sensitivity negative emulsions, low-sensitivity positive emulsions, orthochromatic emulsions, or panchromatic emulsions.

The photosensitive silver salt may be of any type such as, for example, silver bromide, silver iodide, silver chloride, mixed halide of silver (e.g. silver chlorobromide and silver iodobromide). The silver halide may be dispersed in common hydrophilic colloids such as, for example, gelatin, casein, polyvinyl alcohol and carboxymethylcellulose, gelatin being most advantageous. The silver halide emulsion may be sensitized either chemically or optically. The chemical sensitization is effected by the ripening in the presence of a small amount of a sulfur-containing compound (e.g. allyl thiocyanate, allylthiourea or sodium thiosulfate). Further, the emulsion can be sensitized with a reducing agent (for example, a tin compound described in French Pat. No. 1,146,955 and U.S. Pat. No. 2,487,850; an iminoaminomethanesulfinic acid compound described in Brit. Pat. No. 789,823) and a small amount of noble metals (for example, gold, platinum, palladium, iridium, ruthenium and rhodium). Further, the emulsion may be sensitized with cyanine and merocyanine dyes.

Other additives such as, for example, development accelerators, sensitizers and antioxidants may be included in the silver halide emulsion layers or other water-permeable colloid layers. Further, the present antifoggant precursors may be used in combination with other antifoggants or antifoggant precursors.

The invention is illustrated below in detail with reference to Examples.

EXAMPLE 1

A silver iodochlorobromide gelatin emulsion of 0.45 μm in average grain size comprising 65.5 mole-% of silver bromide, 34.0 mole-% of silver chloride and 0.5 mole-% of silver iodide was prepared by the neutral single jet process. After physical ripening and subsequent desalting by washing with water, gelatin was added to the emulsion. Then chemical sensitization was effected by adding sodium thiosulfate. The emulsion was finished by adding a sensitizing dye, a stabilizer, a surface active agent, and a hardener. The resulting gelatin silver halide emulsion was divided into 12 portions. To 6 portions were added independently the compounds described above as examples of present antifoggant precursors each in an amount of 2 millimoles for 1 mole of silver halide. To three of the remaining portions, was added 1-phenyl-5-mercaptotetrazole, 2-mercaptobenzothiazole, or 2-mercaptobenzimidazole in an amount of 2 millimoles for each mole of silver halide (Reference A). To two other portions were added the thioethers represented by the following formulas in an amount of 2 millimoles for each mole of silver halide.

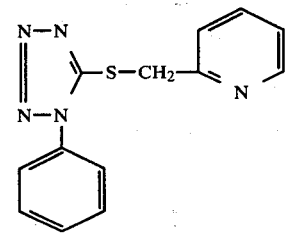

Reference B-1

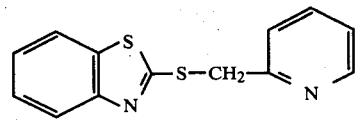

Reference B-2

None was added to the last portion (Reference C).

The 12 emulsions thus obtained were independently coated on polyethylene-coated photographic base paper sheets at a coverage of 2.5 g in terms of silver nitrate and 6.0 g of gelatin per square meter, and dried. The test pieces thus prepared were divided into two groups. The one group was heated at 40° C. for 5 days, while the other was heated for 5 days at 50° C. and 80% relative humidity. A portion of each test piece was exposed through a step optical wedge, developed in a developer of the composition given below, at 20° C. for 120 seconds, then passed through a stopper bath and a fixing bath, washed with water, dried, and tested for photographic characteristics.

| Developer: | |
| --- | --- |
| Water | 750 ml |
| Metol | 1.0 g |
| Hydroquinone | 4.0 g |
| Sodium sulfite | 15.0 g |
| Sodium carbonate monohydrate | 26.7 g |
| Potassium bromide | 0.7 g |
| Water to make up to | 1,000 ml |

The unexposed portion of each test piece was also treated in the same developer at 20° C. for 10 minutes to examine the fogging. The results obtained were as shown in Table 1.

TABLE 1

| Sample No. | Antifoggant precursor (Compound No.) | 40° C., 5 days | | | | 50° C., 80% RH, 5 days | | | |
| --- | --- | --- | --- | --- | --- | --- | --- | --- | --- |
| | | Sensitivity ratio | γ | Max. density | Fog | Sensitivity ratio | γ | Max. density | Fog |
| 1 | 4 | 132.6 | 3.08 | 2.26 | 0.05 | 130.0 | 3.0 | 2.18 | 0.05 |
| 2 | 7 | 130.0 | 3.2 | 2.30 | 0.06 | 129.0 | 3.1 | 2.15 | 0.04 |
| 3 | 11 | 125.5 | 2.96 | 2.25 | 0.04 | 127.3 | 2.9 | 2.20 | 0.05 |
| 4 | 1 | 130.6 | 3.2 | 2.30 | 0.05 | 130.0 | 3.0 | " | 0.04 |
| 5 | 13 | 132.0 | 3.3 | 2.21 | 0.06 | 128.7 | 3.1 | 2.18 | 0.05 |
| 6 | 14 | 126.5 | 2.85 | 2.30 | 0.04 | 125.6 | 2.80 | 2.20 | 0.04 |
| Reference | | | | | | | | | |
| A-1 | 1-Phenyl-5-mercaptotetrazole | 100.0 | 2.8 | 2.10 | 0.04 | 95.0 | 2.73 | 2.00 | 0.03 |
| A-2 | 2-Mercaptobenzothiazole | 98.0 | 2.7 | 2.0 | 0.04 | 93.8 | 2.67 | " | " |
| A-3 | 2-Mercaptobenzimidazole | 95.0 | 2.65 | " | 0.03 | 94.5 | 2.60 | " | " |
| B-1 | Reference B-1 | 133.0 | 3.0 | 2.30 | 0.25 | 135.5 | 2.98 | 2.25 | 0.26 |
| B-2 | Reference B-2 | 132.5 | 2.9 | 2.25 | 0.24 | 135.3 | 2.80 | 2.18 | 0.20 |

TABLE 1-continued

| Sample No. | Antifoggant precursor (Compound No.) | 40° C., 5 days | | | | 50° C., 80% RH, 5 days | | | |
|---|---|---|---|---|---|---|---|---|---|
| | | Sensitivity ratio | γ | Max. density | Fog | Sensitivity ratio | γ | Max. density | Fog |
| C | None | 135.0 | 3.0 | 2.30 | 0.25 | 138.5 | 2.96 | 2.21 | 0.28 |

As is apparent from Table 1, it is seen that the present compound showed very little decrease in maximum density and in contrast (γ value), indicating no adverse effect on photographic characteristics. Since the photographic characteristics were not substantially changed with the change in heating conditions, it is understood that the present antifoggant precursor has undergone no partial hydrolysis during storage. Further, as compared with References B and C, the emulsion containing the present antifoggant precursor showed a fog level as low as that of Reference A, indicating that it had been efficiently hydrolyzed in the developer, releasing the corresponding antifoggant. Moreover, as is apparent from the data on the sensitivity ratio [a relative value of sensitivity as compared with the sensitivity (assumed to be 100.0) of Reference A-1 heated at 40° C. for 5 days], the antifoggant precursor of this invention causes no undesirable decline in sensitivity as compared with References A-1, A-2 and A-3.

EXAMPLE 2

A silver iodochlorobromide gelatin emulsion prepared as in Example 1, was chemically sensitized and finished up by adding thereto a sensitizing dye, stabilizer, surface active agent, and hardener. The resulting gelatin silver halide emulsion was divided into 6 portions. To three of them were added respectively the compounds mentioned previously as examples of antifoggant precursors, each in an amount of 2 millimoles per mole of silver halide. For comparison, one of the remaining three portions of emulsion was incorporated with 1-phenyl-5-mercaptotetrazole (Reference A) and another portion with the following antifoggant precursor (Reference B) disclosed in U.S. Pat. No. 3,674,478, each in an amount of 2 millimoles per mole of silver halide:

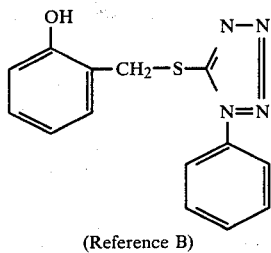

(Reference B)

The last portion of emulsion was used as such without any further additive (Reference C). The antifoggant precursors (or antifoggants) were added to the emulsion just before coating. In order to test the storage stability of the emulsion containing the antifoggant, the remainder of each emulsion after coating was kept at 40° C. and coated on a base sheet at predetermined time intervals. The coating of the emulsion was performed in the same manner as in Example 1. Each coated test piece was kept at 40° C. for 5 days and examined for photographic characteristics and fog density as in Example 1. The results obtained were as shown in Table 2.

TABLE 2

| Sample No. | Antifoggant precursor (Compound No.) | Storage stability of emulsion | | | | | |
|---|---|---|---|---|---|---|---|
| | | Coated immediately after addition | | Coated after 1 hour | | Coated after 4 hours | |
| | | Sensitivity ratio | Fog | Sensitivity ratio | Fog | Sensitivity ratio | Fog |
| 1 | 4 | 132.5 | 0.05 | 132.0 | 0.05 | 130.5 | 0.05 |
| 2 | 7 | 130.0 | 0.06 | 129.5 | 0.06 | 129.0 | 0.05 |
| 3 | 11 | 125.5 | 0.04 | 125.0 | 0.04 | 125.0 | 0.04 |
| | Reference | | | | | | |
| 4 | A | 100.0 | 0.04 | 99.8 | 0.04 | 99.6 | 0.04 |
| 5 | B | 130.0 | 0.07 | 120.5 | 0.06 | 108.3 | 0.05 |
| 6 | C | 135.0 | 0.27 | 136.5 | 0.28 | 138.0 | 0.29 |

Note: Sensitivity ratio:
A relative value of sensitivity as compared with the sensitivity (assumed to be 100.0) of Reference A coated immediately after the addition of antifoggant.

As is apparent from Table 2, the antifoggant precursor of this invention is also excellent in storage stability of the emulsion (stability of the emulsion as a function of time) containing it.

What is claimed is:

1. In a silver halide photograph photosensitive material which comprises a support and at least one photographic layer provided thereon, the improvement which comprises including in at least one of silver halide emulsion layers and colloid layers permeable to water through to or out from said emulsion layer at least one development fog inhibiting compound represented by the following general formula (I):

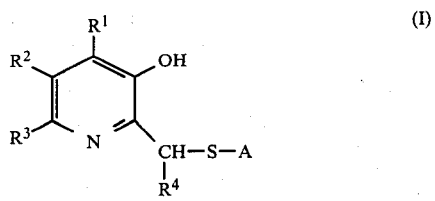

wherein A represents the heterocyclic group of a mercapto-antifoggant; $R^1$, $R^2$ and $R^3$ represent each a hydrogen atom, halogen atom, alkyl group, or phenyl group; $R^1$ and $R^2$, or $R^2$ and $R^3$ may be bonded to each other to form a benzene ring; and $R^4$ represents a hydrogen atom, alkyl group, or phenyl group.

2. A silver halide emulsion which contains a least one development fog inhibiting compound represented by the following general formula (I):

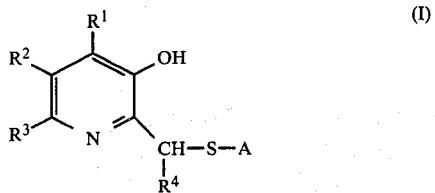

wherein A represents the heterocyclic group of a mercapto-antifoggant; $R^1$, $R^2$ and $R^3$ represent each a hydrogen atom, halogen atom, alkyl group, or phenyl group; $R^1$ and $R^2$, or $R^2$ and $R^3$ may be bonded to each other to form a benzene ring; and $R^4$ represents a hydrogen atom, alkyl group, or phenyl group.

3. A process for forming images which comprises imagewise exposing a silver halide photographic photosensitive material which contains in at least one of silver halide emulsion layers and colloid layers permeable to water through to or out from said emulsion layer at least one development fog inhibiting compound represented by the following general formula (I):

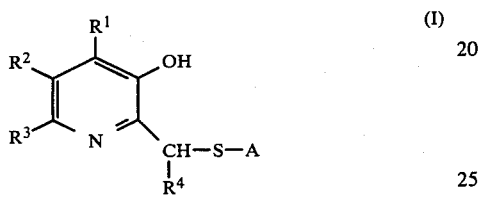

(I)

wherein A represents the heterocyclic group of a mercapto-antifoggant; $R^1$, $R^2$ and $R^3$ represent each a hydrogen atom, halogen atom, alkyl group, or phenyl group; $R^1$ and $R^2$, or $R^2$ and $R^3$ may be bonded to each other to form a benzene ring; and $R^4$ represents a hydrogen atom, alkyl group or phenyl group and then developing the exposed photosensitive material.

4. A silver halide photographic photosensitive material according to claim 1 wherein the amount of said compound is at least 0.1 millimole per mole of silver halide.

5. A silver halide photograph photosensitive material according to claim 4 wherein the amount of said compound is 0.1 to 100 millimoles per mole of silver halde.

6. A silver halide photograph photosensitive material according to claim 4 wherein said compound is

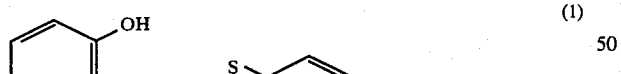

(1)

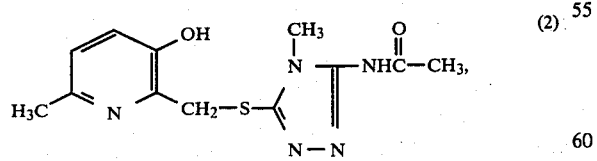

(2)

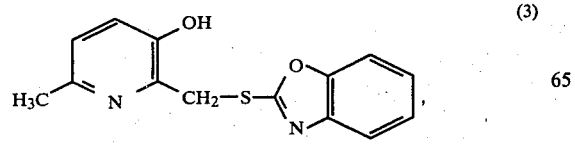

(3)

-continued

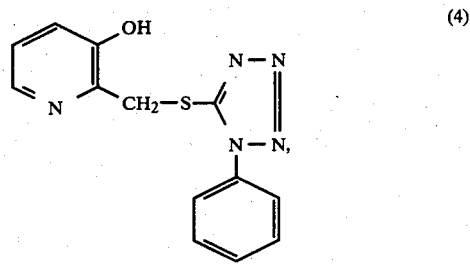

(4)

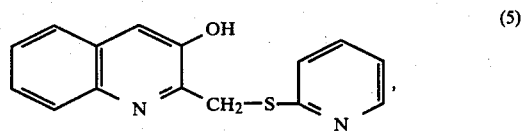

(5)

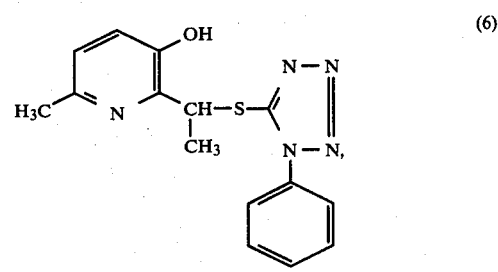

(6)

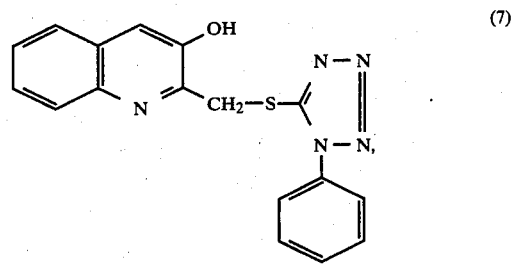

(7)

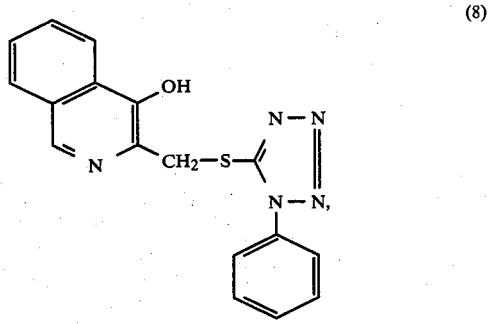

(8)

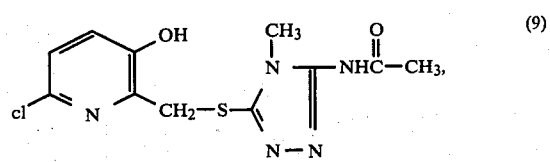

(9)

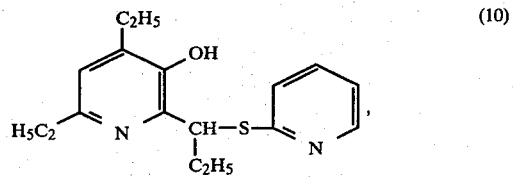

(10)

-continued
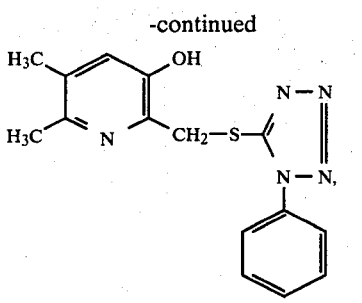 (11)
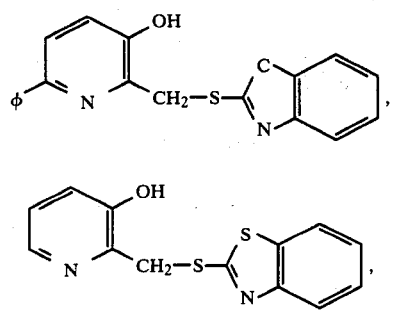 (12)
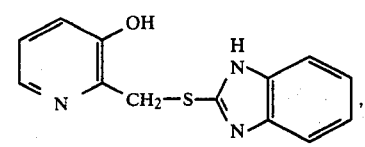 (13)
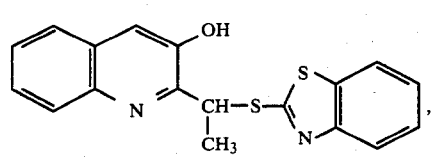 (14)
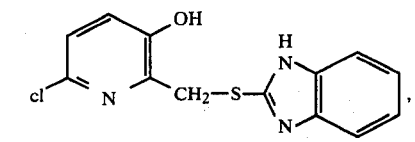 (15)
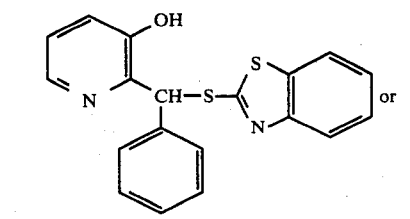 (16)
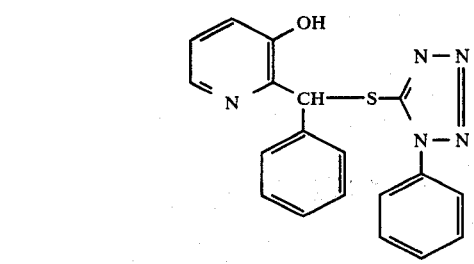 or (17)
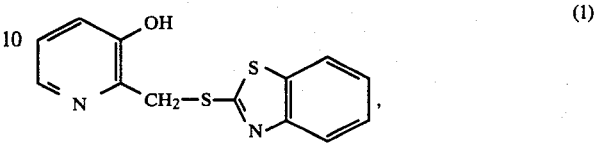 (18)
7. A silver halide emulsion according to claim 2 wherein the amount of said compound is at least 0.1 millimole per mole of silver halide.
8. A silver halide emulsion according to claim 7 wherein the amount of said compound is 0.1 to 100 millimoles per mole of silver halide.
9. A silver halide emulsion according to claim 7 wherein said compound is
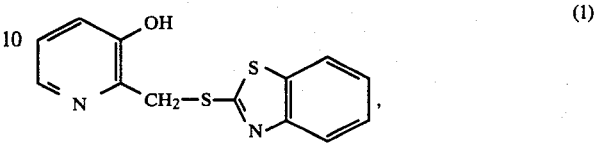 (1)
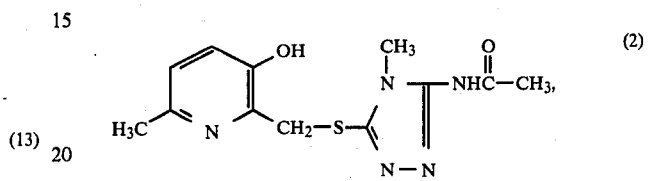 (2)
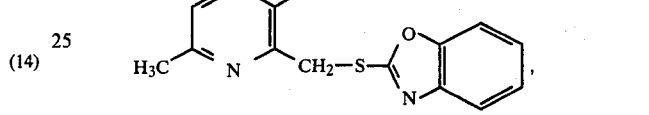 (3)
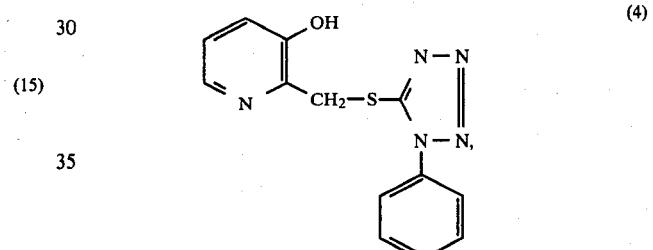 (4)
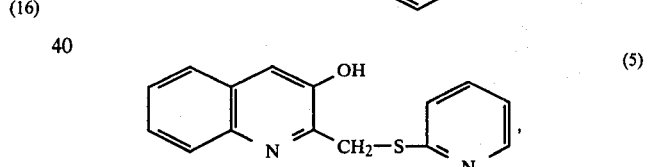 (5)
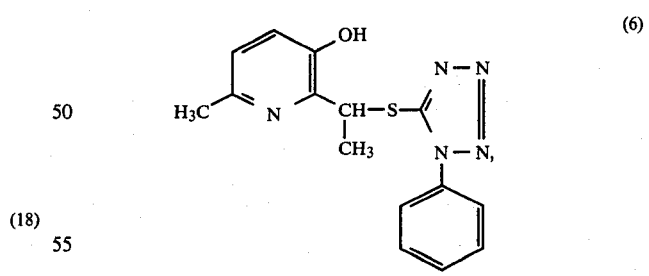 (6)
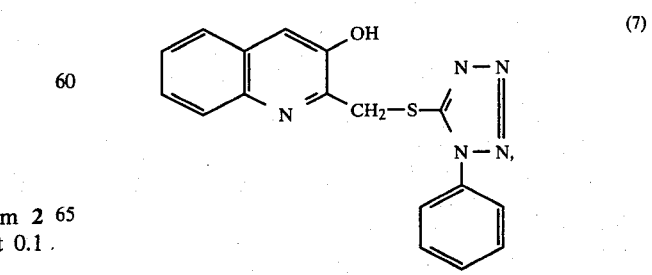 (7)

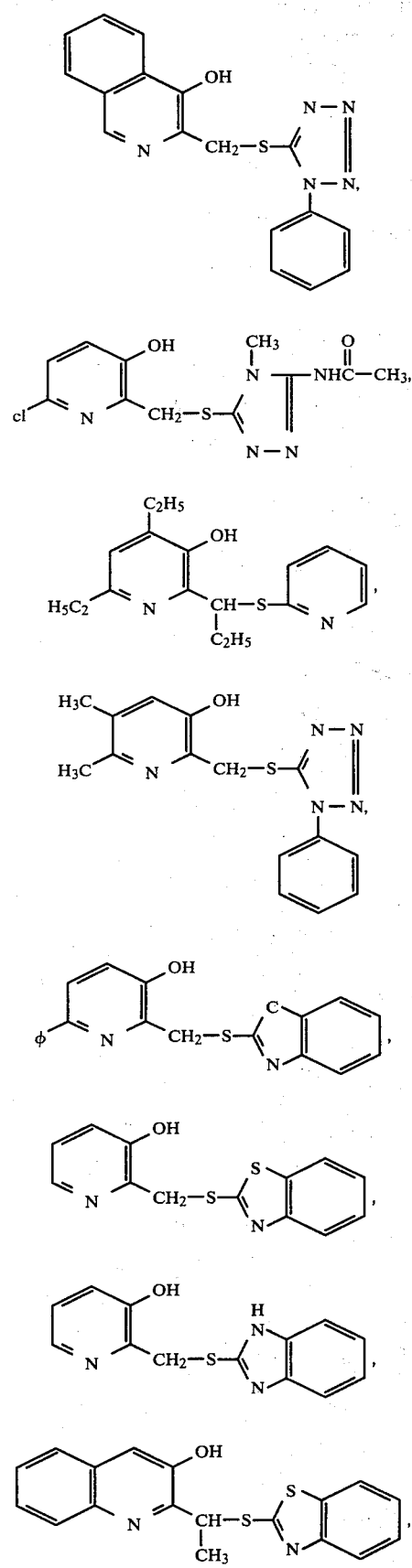
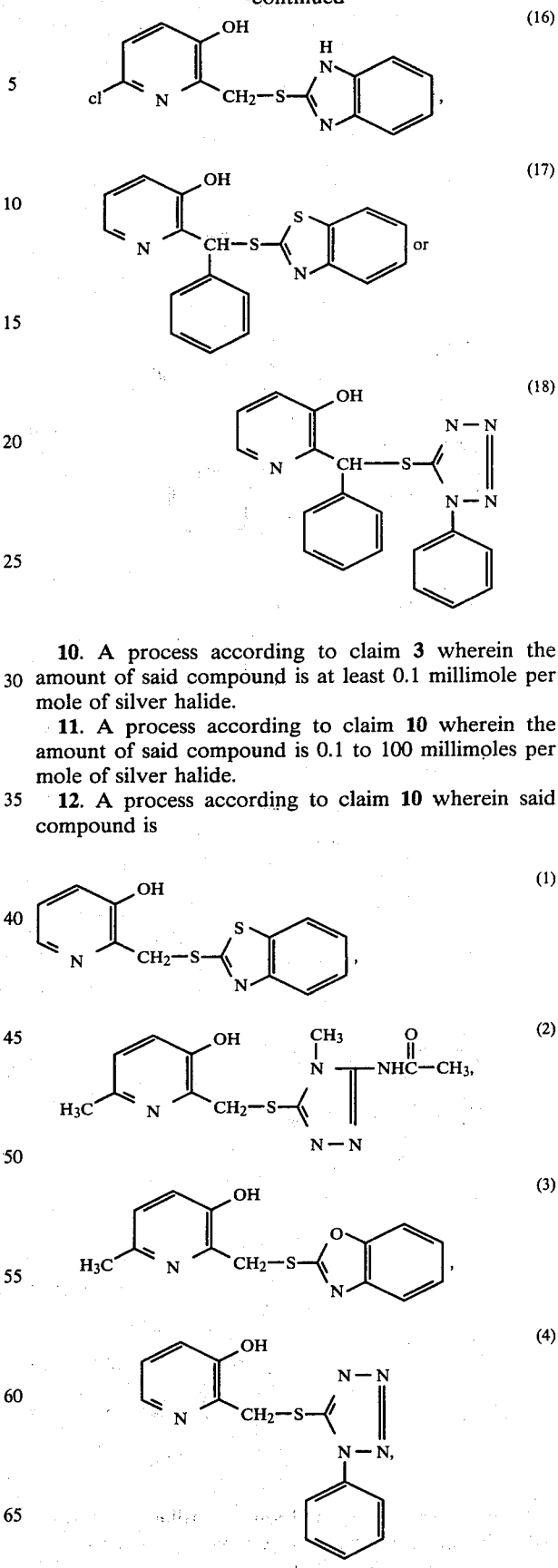
10. A process according to claim 3 wherein the amount of said compound is at least 0.1 millimole per mole of silver halide.
11. A process according to claim 10 wherein the amount of said compound is 0.1 to 100 millimoles per mole of silver halide.
12. A process according to claim 10 wherein said compound is -continued
(5) 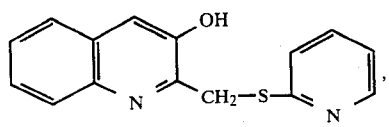
(6) 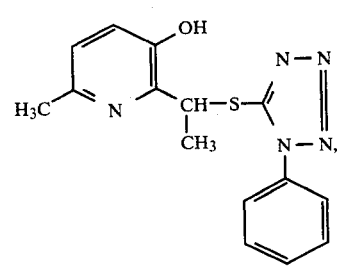
(7) 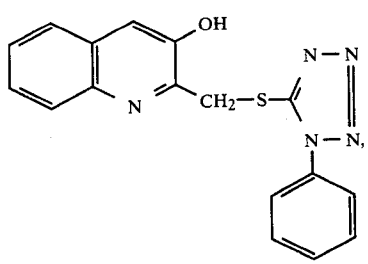
(8) 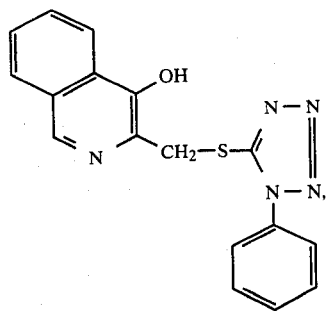
(9) 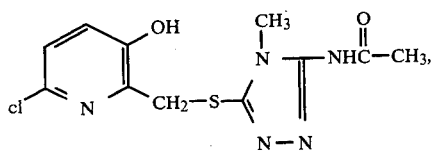
(10) 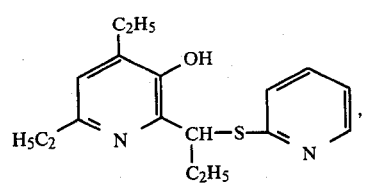
-continued
(11) 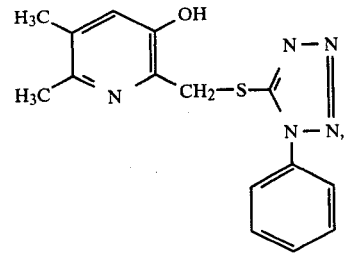
(12) 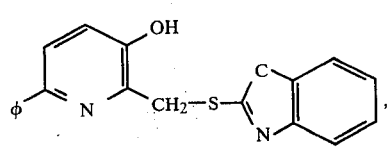
(13) 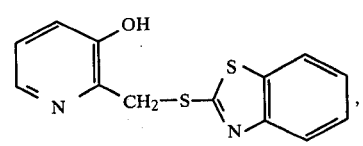
(14) 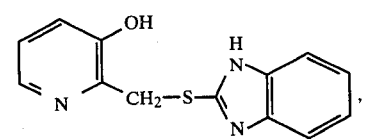
(15) 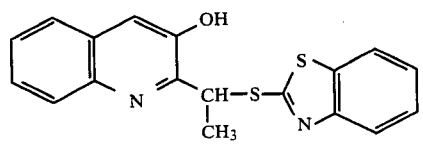
(16) 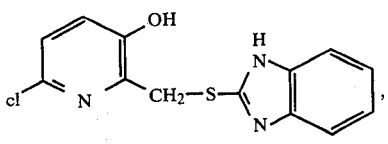
(17) 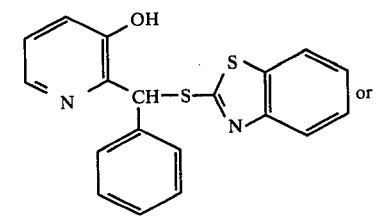 or
(18) 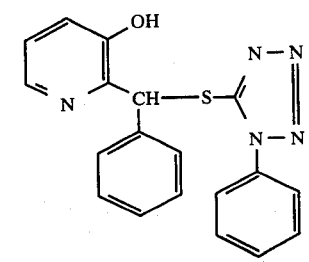
* * * * *